(12) United States Patent
Carter et al.

(10) Patent No.: US 8,524,504 B2
(45) Date of Patent: Sep. 3, 2013

(54) SENSOR

(75) Inventors: Timothy Joseph Nicholas Carter, Sheerness (GB); Steven Andrew Ross, Ashford (GB)

(73) Assignee: Vivacta Limited, Sittingbourne, Kent (GB)

( * ) Notice: Subject to any disclaimer, the term of this patent is extended or adjusted under 35 U.S.C. 154(b) by 442 days.

(21) Appl. No.: 12/675,684

(22) PCT Filed: Aug. 13, 2008

(86) PCT No.: PCT/GB2008/050699
§ 371 (c)(1),
(2), (4) Date: Jul. 8, 2010

(87) PCT Pub. No.: WO2009/027726
PCT Pub. Date: Mar. 5, 2009

(65) Prior Publication Data
US 2010/0285609 A1 Nov. 11, 2010

Related U.S. Application Data

(60) Provisional application No. 60/969,309, filed on Aug. 31, 2007.

(30) Foreign Application Priority Data

Aug. 31, 2007 (GB) .................................. 0716968.3

(51) Int. Cl.
*G01N 25/18* (2006.01)
(52) U.S. Cl.
USPC ........... 436/149; 436/501; 436/518; 436/524; 436/528; 435/7.1; 435/283.1; 435/287.2; 435/287.1
(58) Field of Classification Search
USPC .......... 436/501, 518, 524, 528, 149; 435/7.1, 435/283.1, 287.2, 287.1
See application file for complete search history.

(56) References Cited

U.S. PATENT DOCUMENTS 7,169,617 B2 1/2007 Arinaga et al.
8,119,394 B2 * 2/2012 McGrath et al. ........... 435/297.1
(Continued)

FOREIGN PATENT DOCUMENTS

WO 20040090512 A1 10/2004
WO 20050121798 A1 12/2005
(Continued)

OTHER PUBLICATIONS

International Search Report for corresponding PCT application No. PCT/GB2008/050699 dated Feb. 12, 2008.
(Continued)

*Primary Examiner* — Melanie Y Brown
(74) *Attorney, Agent, or Firm* — Wood, Phillips, Katz, Clark & Mortimer

(57) ABSTRACT

This invention relates to a method for detecting an analyte in a sample, comprising the steps of exposing the sample to a transducer which is capable of transducing a change in energy to an electrical signal, the transducer having at least one tethered reagent on or proximal thereto, the at least one tethered reagent having a binding site which is capable of binding the analyte; introducing a labelled reagent into the sample, wherein the labelled reagent contains a binding site for the analyte or the tethered reagent and a label which is capable of absorbing electromagnetic radiation generated by a radiation source to generate energy; allowing the labelled reagent to bind to the analyte or tethered reagent in a first period in which the transducer is oriented such that the labelled reagent is caused to settle, at least in part, on the transducer; subsequently, in a second period, causing the labelled reagent to become unsettled; irradiating the sample with electromagnetic radiation during the first and second periods, transducing the energy generated into an electrical signal; detecting the electrical signal. A device for performing the method is also provided.

23 Claims, 4 Drawing Sheets

(56) References Cited

U.S. PATENT DOCUMENTS

2008/0026451 A1* 1/2008 Braman et al. ............... 435/270
2008/0206104 A1* 8/2008 Prins et al. ................ 422/82.01

FOREIGN PATENT DOCUMENTS

| WO | 20060079795 A1 | 8/2006 |
| WO | 20070107716 A1 | 9/2007 |
| WO | 20070129064 A1 | 11/2007 |
| WO | 20070141581 A1 | 12/2007 |

OTHER PUBLICATIONS

UK Search Report for corresponding priority application No. GB0716968.3 dated Dec. 31, 2007.
International Preliminary Report on Patentability for corresponding PCT application No. PCT/GB2008/050699 dated Aug. 7, 2009.
Gibson, C A., et al., Kinetic factors in the response of piezo-optical chemical monitoring devices, Sensors and Actuators B 51 (1998) 238-243.

* cited by examiner

SENSOR

FIELD OF THE INVENTION

The present invention relates to a sensor and in particular to a sensor and a method for using a sensor to perform a binding assay.

BACKGROUND OF THE INVENTION

In a binding assay, such as an immunoassay, use is made of the specific "lock-and-key" interaction between the analyte (frequently a protein or hapten) and a binding moiety (such as an antibody) specifically directed against all or part (an epitope) of the antigen (the analyte). The binding between the analyte and the antibody is specific, minimising interactions with related but non-identical species, and strong, giving good sensitivity. In order to quantitate the unknown analyte, a fixed amount of either the analyte labelled with a characteristic marker (e.g. a fluorescent or chemiluminescent molecule) or a second antibody (the "reporter") similarly labelled, is mixed with the sample. The labelled species, present in excess, will then bind to the analyte ultimately reaching an equilibrium in which the majority of the analyte is associated with at least one label. Since the concentration of label is fixed, in order to quantitate the analyte, that part associated with the analyte (the "bound" fraction) must be physically separated from that unassociated (the "free" fraction). Either fraction can then be quantitated, the "bound" being directly proportional and the "free" being inversely proportional to the concentration of the analyte. Commonly, the separation of "bound" and "free" fractions is accomplished by using a second antibody (the "capture" antibody), directed against a different epitope on the analyte, bound to a solid phase such as a bead or solid surface. This bead or solid surface can then be physically separated from the bulk solution and the measurement carried out, for example, using a fluorimeter if the label is a fluorescent molecule. Several different forms of binding interactions in addition to antibody/antigen interactions can be utilised in binding assays, including but not limited to DNA/DNA, RNA/RNA and aptamer interactions. Alternative embodiments of such assays are known, such as "competitive" assays, where the analyte is mixed with a known quantity of labelled analyte and the two then compete for binding sites. The degree of bound labelled analyte is then inversely proportional to the amount of unlabelled analyte in the original sample.

A unique way of distinguishing between the "bound" labelled fraction and the "free" labelled fraction without having to perform separation and washing steps is that described in WO 2004/090512, in which the solid-phase incorporating the capture antibody is a piezo- or pyroelectric film, typically PVDF. This has the unique ability to combine the solid-phase separation feature together with the measurement technique. As described in WO 2004/090512 the labelled "reporter" antibody (labelled with a suitable coloured material such as carbon or colloidal gold) binds to the capture surface at a rate proportional to the concentration of the analyte to be measured; this binding is simultaneously monitored by irradiating the surface with light of a complementary colour. Light energy is absorbed by the label on the surface and transferred by non-radiative decay as heat, detected by the PVDF film. A simultaneous benefit of this system is that energy similarly absorbed by unbound label in the bulk solution is lost into the liquid medium without being detected by the PVDF film thus automatically effecting a "separation" between the "bound" and "free" fractions. It is advantageous to use a colloidal particle of sufficient size to allow a significant number of photons to be absorbed by the particle to give a strong signal and hence good sensitivity.

The sensor described in WO 2004/090512 is used to monitor in real time the kinetics of binding of the label to the capture surface, which is proportional to the concentration of the analyte. This method is dependent on the rate of diffusion of the labelled species to the surface and the rate of binding at the surface. If either of these rates is sub-optimal, the overall sensitivity or the reaction time of the assay may be limited. The rate of binding at the surface can be limited by a number of factors, such as steric hindrance between the labelled antibody (for example if a large carbon or gold particle is used as the label). Additionally, there may be electrostatic repulsion which can inhibit the approach of a large (20-500 nm) particle to a solid surface, or there may be orientation effects where the particle approaches the solid phase but the binding surface on the particle is oriented in the wrong direction for binding to take place. This is more likely to occur with large particles coated in many antibodies, with only a small fraction of these antibodies being bound to the analyte, such that only small parts of the surface area of the particle are available to bind to the surface. In addition to these limiting factors on the binding rate, there are also other factors which can limit the size of particle used in an immunoassay test. For example, in conventional "lateral flow" immunochromatographic strip tests, the optimum size of colloidal gold particle is around 40 nm, because larger particles tend to get trapped in the flow membrane due to their size and density. Finally, larger particles have lower diffusion rates and thus take longer to diffuse to the capture surface, thus possibly limiting available signal.

There remains a need in the art, therefore, for further improvements in the sensitivity of such assays.

BRIEF SUMMARY OF THE INVENTION

Accordingly, the present invention provides a method for detecting an analyte in a sample, comprising the steps of:
exposing the sample to a transducer which is capable of transducing a change in energy to an electrical signal, the transducer having at least one tethered reagent on or proximal thereto, the at least one tethered reagent having a binding site which is capable of binding the analyte;
introducing a labelled reagent into the sample, wherein the labelled reagent contains a binding site for the analyte or the tethered reagent and a label which is capable of absorbing electromagnetic radiation generated by a radiation source to generate energy;
allowing the labelled reagent to bind to the analyte or tethered reagent in a first period in which the transducer is oriented such that the labelled reagent is caused to settle, at least in part, on the transducer;
subsequently, in a second period, causing the labelled reagent to become unsettled; irradiating the sample with electromagnetic radiation during the first and second periods, transducing the energy generated into an electrical signal; detecting the electrical signal.

BRIEF DESCRIPTION OF THE DRAWINGS

The present invention will now be described with reference to the drawings, in which.

DETAILED DESCRIPTION OF THE INVENTION

It has been found that when the transducer is inverted or similarly perturbed, any labelled "reporter" not bound to the surface by specific interaction falls away. Thus, the label in close proximity to the transducer will generate a strong signal when appropriately irradiated whilst label distal to the surface generates a weak or negligible signal. There are several advantages to such a system, namely that all of the label can be concentrated near the binding surface, thus increasing the rate of particles binding to the surface. Additionally, driving the particles to the surface under the force of gravity or buoyancy can aid in overcoming any electrostatic repulsion force at the surface if the particle and the surface are of like charge.

Figure 1:
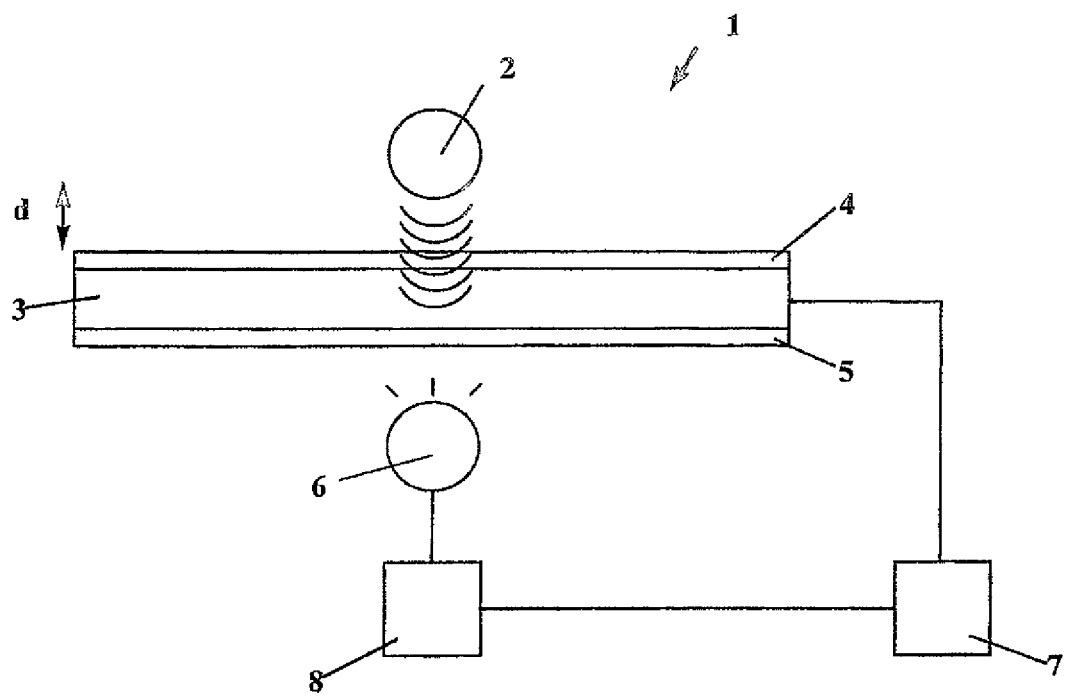
FIG. 1 shows a device according to WO 2004/090512.

The method of the present invention uses a sensor of the type disclosed in WO 90/13017 or WO 2004/090512. FIG. 1 reproduced herein corresponds to FIG. 1 in WO 2004/090512.

As explained in WO 2004/090512, FIG. 1 shows a chemical sensing device 1 of the type used with the present invention. The device 1 relies on heat generation in a substance 2 on irradiation of the substance 2 with electromagnetic radiation. (The substance 2 used in the present invention is actually a labelled reagent on or proximal to the transducer 3 which is discussed in more detail hereinbelow.) The device 1 comprises a transducer, such as a pyroelectric or piezoelectric transducer 3 having electrode coatings 4,5. A substance 2 is held on or proximal to the transducer 3 using any suitable technique. The substance may be in any suitable form and a plurality of substances may be deposited. Preferably, the substance 2 is adsorbed on to the transducer and in particular the upper electrode, e.g. covalently coupled or bound via intermolecular forces such as ionic bonds, hydrogen bonding or van der Waal's forces. The substance 2 generates heat when irradiated by a source of electromagnetic radiation 6, such as light, preferably visible light. The light source may be, for example, an LED. The light source 6 illuminates the substance 2 with light of the appropriate wavelength (e.g. a complementary colour). Although not wishing to be bound by theory, it is believed that the substance 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. As described in WO 2004/090512, the signal from the transducer 3 will depend on the distance of substance 2 from the transducer 3, and the time delay between the light pulse and the signal can give beneficial information on that distance. The device of the present invention is calibrated for the particular substance being measured and hence the precise form of the energy generated does not need to be determined. Unless otherwise specified the term "heat" is used herein to mean the energy generated by non-radiative decay. The light source 6 is positioned so as to illuminate the substance 2. Preferably, the light source 6 is positioned below the transducer 3 and electrodes 4,5 and the substance 2 is illuminated through the transducer 3 and electrodes 4,5. The light source may be an internal light source within the transducer in which the light source is a guided wave system. The wave guide may be the transducer itself or the wave guide may be an additional layer attached to the transducer.

In the method of the present invention, the sample to be analysed is exposed to a transducer 3. As described hereinabove, the transducer 3 is capable of transducing a change in energy to an electrical signal.

The energy generated by the substance 2 is detected by the transducer 3 and converted into an electrical signal. The electrical signal is detected by a detector 7. The light source 6 and the detector 7 are both under the control of the controller 8. The light source 6 preferably generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is at least 2 Hz, more preferably from 2-50 Hz, more preferably 5-15 Hz and most preferably 10 Hz. This corresponds to a time delay between pulses of at most 500 ms, 20-500 ms, 66-200 ms and 100 ms, respectively. However, the time delay may be as low as 1 ms. In addition, the so-called "mark-space" ratio, i.e. the ratio of on signal to off signal is preferably one although other ratios may be used without deleterious effect. Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. This time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

Thus substance 2 may be separated from the transducer surface and a signal may still be detected. Moreover, not only is the signal detectable through an intervening medium capable of transmitting energy to the transducer 3, but different distances, d, may be distinguished (this has been termed "depth profiling") and that the intensity of the signal received is proportional to the concentration of the substance 2 at the particular distance, d, from the surface of the transducer 3.

Accordingly, in a preferred embodiment of the present invention, the sample is irradiated with a series of pulses of electromagnetic radiation and the method further comprising the step of detecting the time delay between each pulse of electromagnetic radiation from the radiation source and the generation of the electric signal, wherein the time delay between each of the pulses of electromagnetic radiation and the generation of the electric signal corresponds to the position of the label at any of one or more positions at different distances from the surface of the transducer. The method of the present invention may thus be carried out without removing the sample from the transducer.

As shown in FIG. 2(a), in the present invention, the transducer 3 is incorporated into a sample chamber 9. The transducer 3 has at least one tethered reagent 10 on or proximal thereto which has a binding site which is capable of binding the analyte 11. For example, the at least one tethered reagent 10 may be an antibody, the analyte 11 may be an antigen, and the labelled reagent may be a labelled antigen which is also capable of binding to the at least one tethered reagent or a labelled antibody which is also capable of binding to the analyte. In this example, when the labelled reagent is a labelled antigen which is also capable of binding to the at least one tethered reagent 10, the electrical signal detected by the detector is inversely proportional to the presence of the analyte in the sample. In another example, the at least one tethered reagent is a first nucleic acid and the analyte is a second nucleic acid and the first and second nucleic acids are complementary. In a further example, the at least one tethered reagent contains avidin or derivatives thereof and the analyte contains biotin or derivatives thereof, or vice versa. Examples of suitable immunoassays are described in WO 2004/090512. Preferably the at least one tethered reagent is adsorbed or covalently bound to the transducer, although other methods for attaching reagents to surfaces are known, which may also be used.

Figure 2:
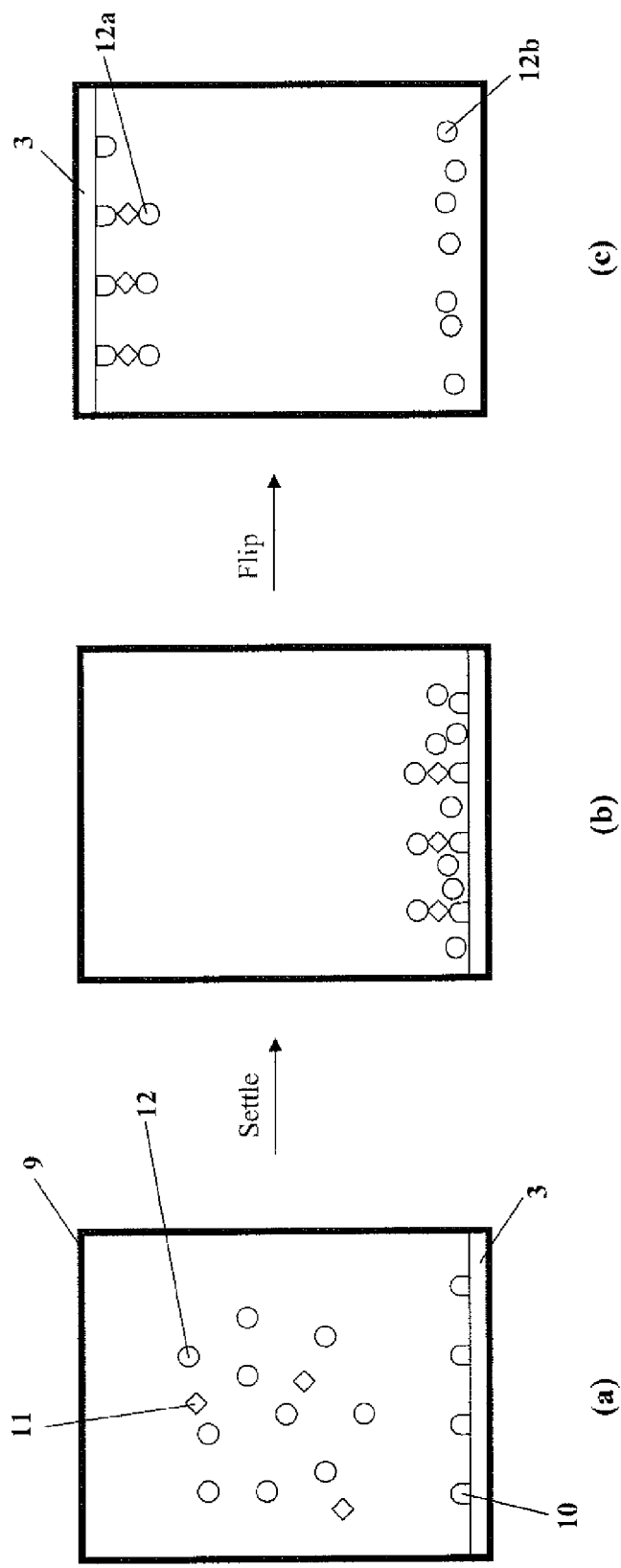
FIG. 2 shows a schematic representation of the method of the present invention.

A labelled reagent 12 is then introduced into the sample. The labelled reagent 12 contains a binding site for the analyte 11 or the tethered reagent 10 and a label which is capable of absorbing electromagnetic radiation generated by a radiation source to generate energy. In FIG. 2(*b*), the labelled reagent 12 binds to the analyte 11.

The sample is then left for sufficient time to allow the labelled reagent 12 to bind to the analyte 11 or tethered reagent 10, here the analyte 11. In this first period of the assay, the transducer is oriented such that gravity acts on the labelled reagent 12 to cause the labelled reagent 12 to settle, at least in part, on the transducer 3.

The label therefore needs to have a sufficient density that it will settle in a reasonable timescale. This will depend on the nature of particle, the nature of sample and the time required to perform the assay. The label is preferably selected from a metal (preferably gold) particle, a coloured-polymer particle (e.g. a coloured latex particle), a magnetic particle, a carbon particle and a nanoparticle comprising a non-conducting core material and at least one metal shell layer (see U.S. Pat. No. 6,344,272). However, any label capable of interacting with electromagnetic radiation to generate heat would be acceptable, providing it absorbs at the appropriate frequency and settles under gravity. In the case of a magnetic particle, the electromagnetic radiation is radio frequency radiation. All of the other labels mentioned hereinabove employ light, which can include IR or UV radiation. In the case of a gold particle, to increase the signal further, the label may be enhanced by catalytic deposition of metallic silver using a solution of silver ions and a reducing agent. The gold catalyses/activates the reduction of the silver ions to silver metal and it is the silver metal which absorbs the light. Preferably the label is a gold particle. Gold particles are commercially available or may be prepared using known methods (see for example G. Frens, Nature, 241, 20-22 (1973)).

Preferably, the present invention uses a particle having a particle size of 20 to 1,000 nm, more preferably 100 to 500 nm. By particle size is meant the diameter of the particle at its widest point. Preferably, the particle has a density of 1.5 to 23 g/mL, more preferably 15-20 g/mL and most preferably 19 g/mL. In a particularly preferred embodiment, the particle is a gold particle having the afore-mentioned particle size and density, although other dense materials could be used, such as osmium or iridium. Subsequently, in a second period, the labelled reagent is caused to become unsettled. Unsettling the labelled reagent changes the signal received at the transducer and provides an indication of the amount of labelled reagent which is bound to the tethered reagent. The labelled reagent is preferably caused to become unsettled by inverting or partially inverting the transducer with respect to the sample. By partially inverting is meant that the transducer is inclined such that the labelled reagent is caused to move away from the transducer surface. Alternatively, the labelled reagent may be caused to become unsettled by agitating the sample. However, in either case, unsettling the system causes the unbound label to become separated from the transducer. FIG. 2(*c*) shows the sample chamber 9 after inversion. It can be seen that the bound analyte 11 and the labelled reagent 12*a* which is bound to the analyte 11, remain close (proximal) to the transducer 3 while the unbound labelled reagent 12*b* is remote (distal).

In the method of the present invention, the sample is irradiated with electromagnetic radiation during the first and second periods to allow a comparison between the two. As described hereinabove with reference to WO 2004/090512, the energy generated by the label is transduced into an electrical signal which is then detected by the detector and processed in central processing unit.

The sample is typically a fluid sample, such as a bodily fluid, e.g. serum, plasma or urine.

The transducer is typically part of a sample chamber. In a preferred embodiment, the labelled reagent is releasably attached to one of the interior surfaces of the chamber prior to use. By releasably attached is meant that the labelled reagent is attached to the surface, e.g. by being dried down on to the surface, but is released when the sample is introduced. More preferably, the transducer defines the top of the chamber and the labelled reagent is releasably attached to an interior bottom surface of the chamber. This latter arrangement is particularly suitable for taking a baseline measurement. The baseline measurement is taken after the sample and labelled reagent are presented to the transducer, in such a manner that the labelled reagent is remote from the transducer. At this point, in a sandwich assay, it is possible that the analyte may bind to the tethered reagent or to the labelled reagent, however the formation of the sandwich at the surface is precluded because the two are distal to each other. In a competitive assay, it is possible that analyte in solution may bind to the tethered reagent, filling up binding sites before the labelled reagent is allowed to move to the transducer. In the example above, where the transducer forms the top of a chamber and the labelled reagent is deposited on the bottom of the chamber, the labelled reagent will remain on the bottom of the chamber under the force of gravity. A baseline reading is taken and the chamber is inverted allowing the labelled reagent to settle on the transducer where a measurement can be taken by following the method described herein. Thus, the sample is introduced thereby releasing the labelled reagent, a baseline measurement is taken, the chamber is inverted or partially inverted to allow the labelled reagent to settle, at least in part, on the transducer. After sufficient time to allow the sedimentation to occur, the chamber is inverted once more, back to its original position. This then allows unbound labelled reagent to sediment away from the surface, leaving the bound fraction to be quantitated.

The present invention has been described with reference to a labelled reagent which is more dense than the liquid medium of the sample so that the labelled reagent settles towards the transducer forming the lower surface (the base) of the sample chamber in the first part of the assay and away from the transducer in the second. That is, the labelled reagent is more dense than the sample and gravity acts on the labelled reagent to cause the labelled reagent to settle, at least in part, on the transducer. Alternatively, the labelled reagent may be less dense than the liquid medium of the sample so that the labelled reagent settles towards the transducer forming the upper surface of the sample chamber (the lid) in the first part of the assay and away from the transducer in the second. That is, the labelled reagent floats to the upper part of the sample chamber under the force of buoyancy. Thus, the labelled reagent is less dense than the sample and buoyancy acts on the labelled reagent to cause the labelled reagent to settle, at least in part, on the transducer. Whether the labelled reagent settles by sedimentation or by floatation, the labelled reagent will have a different density to the sample.

The present invention also provides a device and kit for performing the above-described method. The device may take the form of a hand-held portable reader and a disposable device containing the transducer.

The sample is collected in an essentially closed system, mixed with the labelled reagent and placed in a reader that would orient the analytical chamber as appropriate for capture and then allow the excess unbound labelled reagent to fall/float away. Typically, this involves a rotating cassette within a stationary reader, although physically turning the reader may also be included. In such a device, the chamber is sealed or at least the sample is sufficiently constrained to prevent its leaving the chamber during reorientation, for example by surface tension forces inside a capillary channel.

Accordingly, the present invention also provides a device for detecting an analyte in a sample comprising a radiation source adapted to generate electromagnetic radiation;

a transducer capable of transducing a change in energy to an electrical signal;

at least one tethered reagent on or proximal to the transducer, the tethered reagent having a binding site which is capable of binding the analyte;

a chamber for holding the sample in fluid contact with transducer, wherein the chamber is adapted to contain the sample on inversion, partial inversion or agitation of the device; and a detector which is capable of detecting the electrical signal generated by the transducer.

Preferably the transducer is adapted to undergo inversion, partial inversion or agitation with respect to the sample. In particular the sample chamber is sealed to prevent the sample from spilling. The chamber may be sealed with a lid, or by capillary forces within the sample chamber. Preferably the sample chamber is a capillary tube. The sample chamber preferably has a depth of 50-500 µm, more preferably 100-300 µm, and a length/width of 1-10 mm, more preferably 5 mm, by 10-50 mm, more preferably 30 mm. The sample volume is preferably 1-100 µL, more preferably 10-50 µL, and most preferably about 30 µL.

As described hereinabove, the transducer is preferably a pyroelectric or piezoelectric transducer having a pyroelectric or piezoelectric element and electrodes, and the at least one tethered reagent is preferably adsorbed on to the transducer.

The present invention also provides a kit comprising the device as described herein and the labelled reagent also as described herein.

EXAMPLES

Figure 3:
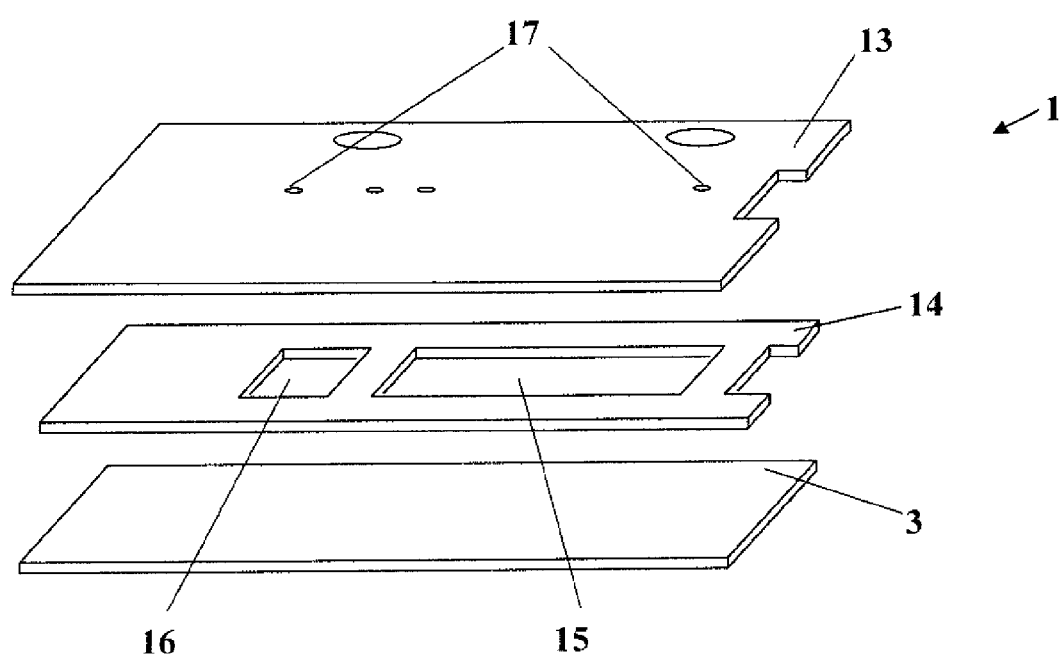
FIG. 3 shows a device according to the present invention.

As shown in FIG. 3, a sensor 1 is fabricated from a transducer 3 which is composed of a piece of poled piezoelectric polyvinylidene fluoride coated in indium tin oxide and a piece of transparent polycarbonate lidding film 13. The transducer 3 is coated in antibodies directed against thyroid stimulating hormone (TSH), using standard methods known in the art. The transducer 3, which has a thickness of approximately 100 microns, and the lidding material 13 are spaced at a distance of approximately 500 microns using a spacer 14 composed of a piece of polyester coated in pressure sensitive adhesive. This creates a larger sample chamber 15 of approx dimensions 30×10×0.5 mm. A second smaller chamber 16 is fabricated of dimensions 10×10×0.5 mm to allow for a control reaction. Provision is made to allow for electrical connections to the top and bottom surfaces of the transducer 3 in order to detect the charge generated.

Figure 4:
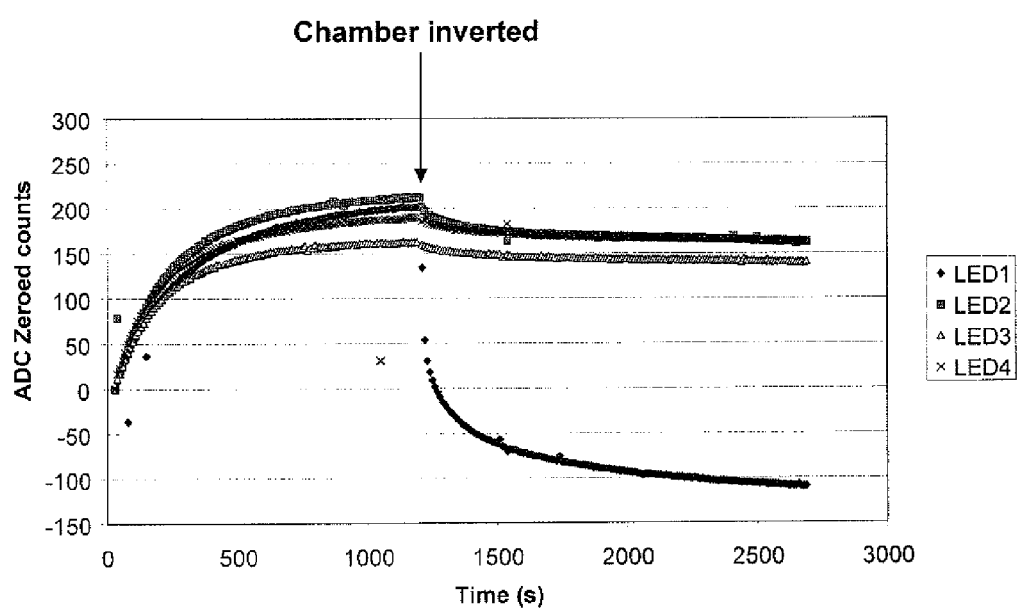
FIG. 4 shows a graph of counts against time, using the method of the present invention.

Assays are carried out by filling the larger chamber 15 (through a fill hole 17) with a mixture of buffer containing 200 nm colloidal gold particles coated with antibodies to TSH and also with TSH at a concentration of 5 ng/mL. The control chamber 16 is simultaneously filled with just buffer and gold particles (at identical concentrations) but no TSH. The entry and exit holes are sealed, then the chamber assembly is connected to a test instrument such that the piezofilm 3 is oriented horizontally on the bottom face of the chamber. The piezofilm 3 is then illuminated with chopped LED light sequentially with four LEDs (of wavelength 525 nm), of which three illuminate different areas of the surface of the read chamber and one illuminates the piezofilm surface of the control chamber 16. For each LED pulse, a voltage is measured across the piezofilm 3 using a lock-in amplifier and analogue to digital (ADC) converter. The ADC signal is plotted over time and is shown in FIG. 4. It can be observed that the ADC signal rises over the first 1200 seconds, which represents the increased thermal stress induced in the piezofilm 3 as the illuminated gold particles sediment to the surface of the film. After 1200 seconds the signals from the control chamber (LED 1) and the measurement chamber (LEDs 2, 3 and 4) are indistinguishable.

At this point the chamber is inverted, such that the piezofilm 3 now forms the top or "roof" of the chamber (this corresponds to the position in FIG. 2(c)). It can be observed that the signal in the control chamber (LED 1) falls rapidly as the gold particles move away from the surface under the force of gravity. However, in the measurement chamber (LEDs 2, 3 and 4), the fall in signal is much less pronounced, because the TSH present in the sample bridges between the antibodies on the gold particles and the antibodies on the surface, causing the gold particles to be bound to the surface of the piezofilm 3.

The difference between these plots can be used to confirm that TSH was present in the reaction mixture. Additionally, by preparing a calibration curve using different concentrations of TSH it is possible to use this system as a quantitative test for TSH concentrations in human fluids.

We claim:

1. A method for detecting an analyte in a sample, comprising the steps of:

exposing the sample to a transducer which is capable of transducing a change in energy to an electrical signal, the transducer having at least one tethered reagent on or proximal thereto, the at least one tethered reagent having a binding site which is capable of binding the analyte;

introducing a labelled reagent into the sample, wherein the labelled reagent contains a binding site for the analyte or the tethered reagent and a label which is capable of absorbing electromagnetic radiation generated by a radiation source to generate energy; allowing the labelled reagent to bind to the analyte or tethered reagent in a first period in which the transducer is oriented such that the labelled reagent is caused to settle, at least in part, on the transducer;

subsequently, in a second period, causing unbound labelled reagent to become unsettled by inverting or partially inverting the transducer with respect to the sample; irradiating the sample with electromagnetic radiation during the first and second periods, transducing the energy generated into an electrical signal;

detecting the electrical signal generated by bound labeled reagent to indicate the analyte in the sample.

2. A method as claimed in claim 1, wherein the labelled reagent is more dense than the sample and gravity acts on the labelled reagent to cause the labelled reagent to settle, at least in part, on the transducer.

3. A method as claimed in claim 1, wherein the labelled reagent is less dense than the sample and buoyancy acts on the labelled reagent to cause the labelled reagent to settle, at least in part, on the transducer.

4. A method as claimed in claim 1, wherein the transducer is a pyroelectric or piezoelectric transducer having a pyroelectric or piezoelectric element and electrodes.

5. A method as claimed in claim 1, wherein the label generates energy on irradiation by non-radiative decay.

6. A method as claimed claim 1, wherein the sample is irradiated with a series of pulses of electromagnetic radiation and the method further comprising the step of detecting the time delay between each pulse of electromagnetic radiation from the radiation source and between each of the pulses of electromagnetic radiation and the generation of the electric signal corresponds to the position of the label at any of one or more positions at different distances from the surface of the transducer.

7. A method as claimed in claim 6, wherein the frequency of the pulses of electromagnetic radiation is at least 2 Hz.

8. A method as claimed in claim 6, wherein the time delay is from 1 to 500 milliseconds.

9. A method as claimed in claim 6, wherein the electromagnetic radiation is light, preferably visible light.

10. A method as claimed in claim 1, wherein the at least one tethered reagent is an antibody, the analyte is an antigen, and the labelled reagent is a labelled antigen which is also capable of binding to the at least one tethered reagent or a labelled antibody which is also capable of binding to the analyte.

11. A method as claimed in claim 1, wherein the at least one tethered reagent is a first nucleic acid and the analyte is a second nucleic acid and the first and second nucleic acids are complementary.

12. A method as claimed in claim 1, wherein the at least one tethered reagent contains avidin or derivatives thereof and the analyte contains biotin or derivatives thereof, or vice versa.

13. A method as claimed in claim 1, wherein the at least one tethered reagent is adsorbed on to the transducer.

14. A method as claimed in claim 1, wherein the label is a particle having a particle size of 20-1,000 nm.

15. A method as claimed in claim 1, wherein the label is a particle having a density of 1.5 to 23 g/ml.

16. A method as claimed in claim 1, wherein the label on the labelled reagent is selected from a metal particle, a coloured-polymer particle, a magnetic particle, a carbon particle, and a nanoparticle comprising a non-conducting core material and at least one metal shell layer.

17. A method as claimed in claim 16, wherein the label is a gold particle.

18. A method as claimed in claim 17, wherein the signal is enhanced by catalytic deposition of metallic silver.

19. A method as claimed in claim 1, wherein a baseline measurement is taken after introducing the labelled reagent into the sample, but before allowing the labelled reagent to settle on the transducer.

20. A method as claimed in claim 1, wherein the transducer is part of a sample chamber and the labelled reagent is releasably attached to one of the interior surfaces of the chamber prior to use.

21. A method as claimed in claim 20, wherein the transducer defines the top of the chamber and the labelled reagent is releasably attached to an interior bottom surface of the chamber.

22. A method as claimed in claim 21, wherein a sample is introduced thereby releasing the labelled reagent, a baseline measurement is taken, the transducer is inverted or partially inverted to allow the labelled reagent to settle, at least in part, on the transducer.

23. A method as claimed in claim 1, wherein a plurality of analytes are detected in the same sample.

* * * * *